US008831720B2

(12) United States Patent
Bardy et al.

(10) Patent No.: US 8,831,720 B2
(45) Date of Patent: Sep. 9, 2014

(54) METHOD OF IMPLANTING AND USING A SUBCUTANEOUS DEFIBRILLATOR

(71) Applicant: Cameron Health, Inc., San Clemente, CA (US)

(72) Inventors: Gust H. Bardy, Seattle, WA (US); Riccardo Cappato, Ferrara (IT)

(73) Assignee: Cameron Health, Inc., St. Paul, MN (US)

( * ) Notice: Subject to any disclaimer, the term of this patent is extended or adjusted under 35 U.S.C. 154(b) by 0 days.

(21) Appl. No.: 14/063,255

(22) Filed: Oct. 25, 2013

(65) Prior Publication Data

US 2014/0052205 A1 Feb. 20, 2014

Related U.S. Application Data

(60) Division of application No. 13/286,673, filed on Nov. 1, 2011, now Pat. No. 8,577,454, which is a continuation of application No. 12/781,668, filed on May 17, 2010, now Pat. No. 8,090,438, which is a continuation of application No. 11/529,671, filed on Sep. 28, 2006, now Pat. No. 7,720,534, which is a continuation of application No. 11/447,711, filed on Jun. 6, 2006, now Pat. No. 7,657,311, which is a continuation of application No. 10/790,903, filed on Mar. 1, 2004, now Pat. No. 7,076,294, which is a continuation of application No. 09/663,607, filed on Sep. 18, 2000, now Pat. No. 6,721,597.

(51) Int. Cl.
*A61N 1/39* (2006.01)
*A61N 1/375* (2006.01)
*A61N 1/365* (2006.01)
*A61B 5/042* (2006.01)

(52) U.S. Cl.
CPC .............. *A61N 1/3956* (2013.01); *A61N 1/375* (2013.01); *A61N 1/3906* (2013.01); *A61N 1/3756* (2013.01); *A61N 1/36521* (2013.01); *A61B 5/042* (2013.01)

USPC ................................. 607/5; 607/119; 607/129

(58) Field of Classification Search
None
See application file for complete search history.

(56) References Cited

U.S. PATENT DOCUMENTS 3,566,860 A 3/1971 Moe, Jr. et al.
3,593,718 A 7/1971 Krasner
(Continued)

FOREIGN PATENT DOCUMENTS

DE 3937594 A1 5/1991
EP 0134367 A1 3/1985
(Continued)

OTHER PUBLICATIONS

"U.S. Appl. No. 13/286,673, Notice of Allowance mailed Jul. 2, 2013", 12 pgs.

(Continued)

*Primary Examiner* — Brian T Gedeon
(74) *Attorney, Agent, or Firm* — Schwegman, Lundberg & Woessner P.A.

(57) ABSTRACT

A subcutaneous implantable cardioverter-defibrillator is disclosed which has an electrically active canister which houses a source of electrical energy, a capacitor, and operational circuitry that senses the presence of potentially fatal heart rhythms. At least one subcutaneous electrode that serves as the opposite electrode from the canister is attached to the canister via a lead system. Cardioversion-defibrillation energy is delivered when the operational circuitry senses a potentially fatal heart rhythm. There are no transvenous, intracardiac, or epicardial electrodes. A method of subcutaneously implanting the cardioverter-defibrillator is also disclosed as well as a kit for conducting the method.

6 Claims, 6 Drawing Sheets

(56) References Cited

U.S. PATENT DOCUMENTS

| | | |
|---|---|---|
| 3,598,128 A | 8/1971 | Chardack |
| 3,707,974 A | 1/1973 | Raddi |
| 3,713,449 A | 1/1973 | Mulier |
| 3,737,897 A | 6/1973 | Cuthbert et al. |
| 3,807,411 A | 4/1974 | Harris et al. |
| 3,822,707 A | 7/1974 | Adducci et al. |
| 3,827,046 A | 7/1974 | Watson et al. |
| 3,828,766 A | 8/1974 | Krasnow |
| 3,841,312 A | 10/1974 | Corasanti |
| 3,842,842 A | 10/1974 | Kenny |
| 3,866,616 A | 2/1975 | Purdy et al. |
| 3,908,668 A | 9/1975 | Bolduc |
| 3,941,135 A | 3/1976 | von Sturm et al. |
| 3,951,154 A | 4/1976 | Hartlaub et al. |
| 3,999,555 A | 12/1976 | Person |
| 4,010,758 A | 3/1977 | Rockland et al. |
| 4,010,759 A | 3/1977 | Boer |
| 4,013,081 A | 3/1977 | Kolenik |
| 4,057,067 A | 11/1977 | Lajos |
| 4,057,068 A | 11/1977 | Comben |
| 4,127,134 A | 11/1978 | Ushakoff |
| 4,141,752 A | 2/1979 | Shipko |
| 4,166,465 A | 9/1979 | Esty et al. |
| 4,236,525 A | 12/1980 | Sluetz et al. |
| 4,256,115 A | 3/1981 | Bilitch |
| 4,270,549 A | 6/1981 | Heilman |
| 4,290,430 A | 9/1981 | Bihn et al. |
| 4,335,756 A | 6/1982 | Sharp et al. |
| 4,349,030 A | 9/1982 | Belgard et al. |
| 4,351,345 A | 9/1982 | Carney |
| 4,354,509 A | 10/1982 | Strahwald et al. |
| 4,406,286 A | 9/1983 | Stein |
| 4,412,541 A | 11/1983 | Schaldach et al. |
| 4,498,478 A | 2/1985 | Bourgeois |
| 4,543,956 A | 10/1985 | Herscovici |
| 4,553,554 A | 11/1985 | Lemole |
| 4,574,800 A | 3/1986 | Peers-trevarton |
| 4,628,937 A | 12/1986 | Hess et al. |
| 4,686,988 A | 8/1987 | Sholder |
| 4,757,817 A | 7/1988 | Healy et al. |
| 4,821,724 A | 4/1989 | Whigham et al. |
| 4,825,871 A | 5/1989 | Cansell |
| 4,827,932 A | 5/1989 | Ideker et al. |
| 4,830,006 A | 5/1989 | Haluska et al. |
| 4,865,037 A | 9/1989 | Chin et al. |
| 4,878,497 A | 11/1989 | Callaghan et al. |
| 4,901,079 A | 2/1990 | Nagashima et al. |
| 4,940,054 A | 7/1990 | Grevis et al. |
| 4,969,463 A | 11/1990 | Dahl et al. |
| 5,003,990 A | 4/1991 | Osypka |
| 5,018,522 A | 5/1991 | Mehra |
| 5,020,544 A | 6/1991 | Dahl et al. |
| 5,036,854 A | 8/1991 | Schollmeyer et al. |
| 5,050,600 A | 9/1991 | Parks |
| 5,083,562 A | 1/1992 | De Coriolis et al. |
| 5,107,836 A | 4/1992 | Fenster |
| 5,111,811 A * | 5/1992 | Smits ............................... 607/2 |
| 5,170,784 A | 12/1992 | Ramon et al. |
| 5,235,977 A | 8/1993 | Hirschberg et al. |
| 5,241,690 A | 8/1993 | Larsson et al. |
| 5,241,960 A | 9/1993 | Anderson et al. |
| 5,243,978 A | 9/1993 | Duffin, Jr. |
| 5,261,401 A | 11/1993 | Baker et al. |
| 5,265,623 A | 11/1993 | Kroll et al. |
| 5,269,810 A | 12/1993 | Hull et al. |
| 5,279,293 A | 1/1994 | Andersen et al. |
| 5,292,338 A | 3/1994 | Bardy |
| 5,300,110 A | 4/1994 | Latterell et al. |
| 5,306,261 A | 4/1994 | Alliger et al. |
| 5,306,291 A | 4/1994 | Kroll et al. |
| 5,312,441 A | 5/1994 | Mader et al. |
| 5,314,430 A | 5/1994 | Bardy |
| 5,318,591 A | 6/1994 | Causey, III et al. |
| 5,327,909 A | 7/1994 | Kiser et al. |
| 5,330,505 A | 7/1994 | Cohen |
| 5,342,400 A | 8/1994 | Hirschberg et al. |
| 5,344,430 A | 9/1994 | Berg et al. |
| 5,344,432 A | 9/1994 | Slettenmark et al. |
| 5,354,328 A | 10/1994 | Doan et al. |
| 5,360,442 A | 11/1994 | Dahl et al. |
| 5,366,485 A | 11/1994 | Kroll et al. |
| 5,370,669 A | 12/1994 | Daglow et al. |
| 5,376,104 A | 12/1994 | Sakai et al. |
| 5,383,913 A | 1/1995 | Schiff et al. |
| 5,385,575 A | 1/1995 | Adams |
| 5,391,191 A | 2/1995 | Holmstrom |
| 5,431,681 A | 7/1995 | Helland |
| 5,431,684 A | 7/1995 | Archer et al. |
| 5,431,692 A | 7/1995 | Hansen et al. |
| 5,433,730 A | 7/1995 | Alt |
| 5,441,518 A | 8/1995 | Adams et al. |
| 5,447,519 A | 9/1995 | Peterson |
| 5,470,345 A | 11/1995 | Hassler et al. |
| 5,477,855 A | 12/1995 | Schindler et al. |
| 5,479,503 A | 12/1995 | Fujiwara |
| 5,489,293 A | 2/1996 | Pless et al. |
| 5,507,781 A | 4/1996 | Kroll et al. |
| 5,507,785 A | 4/1996 | Deno |
| 5,509,924 A | 4/1996 | Paspa et al. |
| 5,514,160 A | 5/1996 | Kroll et al. |
| 5,522,853 A | 6/1996 | Kroll |
| 5,531,764 A | 7/1996 | Adams et al. |
| 5,545,188 A | 8/1996 | Bradshaw et al. |
| 5,545,202 A | 8/1996 | Dahl et al. |
| 5,549,615 A | 8/1996 | Hocherl et al. |
| 5,573,003 A | 11/1996 | Mann et al. |
| 5,601,608 A | 2/1997 | Mouchawar |
| 5,606,320 A | 2/1997 | Kleks |
| 5,645,572 A | 7/1997 | Kroll et al. |
| 5,645,586 A | 7/1997 | Meltzer |
| 5,658,325 A | 8/1997 | Augustine |
| 5,662,696 A | 9/1997 | Kroll et al. |
| 5,709,644 A | 1/1998 | Bush |
| 5,718,242 A | 2/1998 | McClure et al. |
| 5,749,904 A | 5/1998 | Gliner et al. |
| 5,755,743 A | 5/1998 | Volz et al. |
| 5,769,874 A | 6/1998 | Dahlberg |
| 5,772,690 A | 6/1998 | Kroll |
| 5,782,891 A | 7/1998 | Hassler et al. |
| 5,797,968 A | 8/1998 | Lopin et al. |
| 5,800,464 A | 9/1998 | Kieval |
| 5,800,470 A | 9/1998 | Stein et al. |
| 5,849,031 A | 12/1998 | Martinez et al. |
| 5,871,506 A | 2/1999 | Mower |
| 5,871,508 A | 2/1999 | Thompson et al. |
| 5,873,897 A | 2/1999 | Armstrong et al. |
| 5,895,414 A | 4/1999 | Sanchez-Zambrano |
| 5,897,585 A | 4/1999 | Williams |
| 5,902,331 A | 5/1999 | Bonner et al. |
| 5,916,238 A | 6/1999 | Hauser et al. |
| 5,928,270 A | 7/1999 | Ramsey, III et al. |
| 5,944,730 A | 8/1999 | Nobles et al. |
| 5,963,429 A | 10/1999 | Chen |
| 5,964,787 A | 10/1999 | Kerver et al. |
| 5,968,079 A | 10/1999 | Warman et al. |
| 5,978,703 A | 11/1999 | Kroll et al. |
| 5,978,705 A | 11/1999 | KenKnight et al. |
| 5,978,707 A | 11/1999 | Krig et al. |
| 5,987,352 A | 11/1999 | Klein et al. |
| 6,006,133 A | 12/1999 | Lessar et al. |
| 6,038,484 A | 3/2000 | Kuzma |
| 6,056,722 A | 5/2000 | Jayaraman |
| 6,076,014 A | 6/2000 | Alt |
| 6,091,989 A | 7/2000 | Swerdlow et al. |
| 6,093,982 A | 7/2000 | Kroll |
| 6,096,063 A | 8/2000 | Lopin et al. |
| 6,112,124 A | 8/2000 | Loeb |
| 6,169,921 B1 | 1/2001 | KenKnight et al. |
| 6,169,923 B1 | 1/2001 | Kroll |
| 6,176,879 B1 | 1/2001 | Reischl et al. |
| 6,187,028 B1 | 2/2001 | Munshi |
| 6,208,895 B1 | 3/2001 | Sullivan et al. |
| 6,241,751 B1 | 6/2001 | Morgan et al. |
| 6,249,707 B1 | 6/2001 | Kohnen et al. |

(56) References Cited

U.S. PATENT DOCUMENTS

| | | | |
|---|---|---|---|
| 6,256,541 | B1 | 7/2001 | Heil et al. |
| 6,256,543 | B1 | 7/2001 | Spence |
| 6,272,379 | B1 | 8/2001 | Fischell et al. |
| 6,272,385 | B1 | 8/2001 | Bishay et al. |
| 6,283,985 | B1 | 9/2001 | Harguth et al. |
| 6,342,041 | B1 | 1/2002 | Saint-Ramon et al. |
| 6,409,675 | B1 | 6/2002 | Turcott |
| 6,445,956 | B1 | 9/2002 | Laird et al. |
| 6,501,983 | B1 | 12/2002 | Natarajan et al. |
| 6,508,771 | B1 | 1/2003 | Padmanabhan et al. |
| 6,519,493 | B1 | 2/2003 | Florio et al. |
| 6,539,257 | B1 | 3/2003 | KenKnight |
| 6,539,260 | B1 | 3/2003 | Schloss |
| 6,647,292 | B1 | 11/2003 | Bardy et al. |
| 6,658,296 | B1 | 12/2003 | Wong et al. |
| 6,711,443 | B2 | 3/2004 | Osypka |
| 6,721,528 | B1 | 4/2004 | Schreieder et al. |
| 6,721,597 | B1 | 4/2004 | Bardy et al. |
| 6,812,842 | B2 | 11/2004 | Dimmer |
| 6,944,498 | B2 | 9/2005 | Owen et al. |
| 6,950,105 | B2 | 9/2005 | Giemborek et al. |
| 6,952,610 | B2 | 10/2005 | Ostroff et al. |
| 6,954,669 | B1 | 10/2005 | Fishler et al. |
| 6,980,856 | B2 | 12/2005 | Sullivan et al. |
| 7,031,774 | B1 | 4/2006 | Doan et al. |
| 7,069,075 | B2 | 6/2006 | Olson |
| 7,103,415 | B2 | 9/2006 | Probst et al. |
| 7,346,392 | B2 | 3/2008 | Kenknight |
| 7,570,997 | B2 | 8/2009 | Lovett et al. |
| 7,627,367 | B2 | 12/2009 | Warren et al. |
| 7,865,233 | B2 | 1/2011 | Haefner |
| 8,718,760 | B2 | 5/2014 | Bardy et al. |
| 2002/0082658 | A1 | 6/2002 | Heinrich et al. |
| 2002/0103507 | A1 | 8/2002 | Helland |
| 2002/0120296 | A1 | 8/2002 | Mech et al. |
| 2002/0147475 | A1 | 10/2002 | Scheiner et al. |
| 2003/0017372 | A1 | 1/2003 | Probst et al. |
| 2003/0125785 | A1 | 7/2003 | Kuzma |
| 2003/0179123 | A1 | 9/2003 | Devilbiss |
| 2004/0093037 | A1 | 5/2004 | Henry |
| 2004/0220641 | A1 | 11/2004 | Wagner et al. |
| 2005/0055056 | A1 | 3/2005 | Olson |
| 2005/0131464 | A1 | 6/2005 | Heinrich et al. |
| 2005/0143776 | A1 | 6/2005 | Brown |
| 2005/0195084 | A1 | 9/2005 | Dimmer et al. |
| 2006/0217770 | A1 | 9/2006 | Olson |
| 2007/0049976 | A1 | 3/2007 | Ni et al. |
| 2008/0140139 | A1 | 6/2008 | Heinrich et al. |
| 2008/0269813 | A1 | 10/2008 | Greenhut et al. |
| 2008/0319503 | A1 | 12/2008 | Honeck et al. |
| 2012/0046705 | A1 | 2/2012 | Bardy et al. |
| 2013/0123870 | A1 | 5/2013 | Heinrich et al. |

FOREIGN PATENT DOCUMENTS

| | | |
|---|---|---|
| EP | 0348708 A2 | 1/1990 |
| EP | 536873 B1 | 9/1997 |
| EP | 1517494 B1 | 6/2009 |
| JP | 4327450 | 6/2009 |
| WO | WO-9220402 A1 | 11/1992 |
| WO | WO-0041766 A1 | 7/2000 |
| WO | WO-0050120 A1 | 8/2000 |
| WO | WO-0143649 A1 | 6/2001 |
| WO | WO-0156166 A2 | 8/2001 |
| WO | WO-0222205 A1 | 3/2002 |
| WO | WO-02068046 A1 | 9/2002 |
| WO | WO-03018121 A2 | 3/2003 |

OTHER PUBLICATIONS

"U.S. Appl. No. 13/286,673, Response filed Jun. 21, 2013 to Restriction Requirement mailed Jun. 3, 2013", 5 pgs.

"U.S. Appl. No. 13/286,673, Restriction Requirement mailed Jun. 3, 2013", 7 pgs.

"U.S. Appl. No. 13/476,940, filed May 21, 2012", 53 pgs.

"U.S. Appl. No. 13/476,940, Preliminary Amendment filed Jun. 20, 2012", 27 pgs.

"U.S. Appl. No. 09/940,266, Advisory Action mailed Jul. 26, 2004", 2 pgs.

"U.S. Appl. No. 09/940,266, Final Office Action mailed Mar. 24, 2004", 7 pgs.

"U.S. Appl. No. 09/940,266, Non Final Office Action mailed Oct. 7, 2003", 18 pgs.

"U.S. Appl. No. 09/940,266, Response filed Feb. 6, 2004 to Non Final Office Action mailed Oct. 7, 2003", 6 pgs.

"U.S. Appl. No. 09/940,266, Response filed Jun. 23, 2004 to Final Office Action mailed Mar. 24, 2004", 11 pgs.

"U.S. Appl. No. 09/940,266, Response filed Aug. 24, 2004 to Advisory Action mailed Jul. 26, 2004", 13 pgs.

"U.S. Appl. No. 09/940,273, Non Final Office Action mailed Jan. 13, 2005", 8 pgs.

"U.S. Appl. No. 09/940,273, Non Final Office Action mailed Feb. 11, 2004", 14 pgs.

"U.S. Appl. No. 09/940,273, Non Final Office Action mailed Jul. 12, 2004", 10 pgs.

"U.S. Appl. No. 09/940,273, Non Final Office Action mailed Oct. 17, 2005", 7 pgs.

"U.S. Appl. No. 09/940,273, Response filed May 11, 2004 to Non Final Office Action mailed Feb. 11, 2004", 43 pgs.

"U.S. Appl. No. 09/940,273, Response filed Jul. 13, 2005 to Non Final Office Action mailed Jan. 13, 2005", 33 pgs.

"U.S. Appl. No. 09/940,273, Response filed Oct. 8, 2004 to Non Final Office Action mailed Jul. 12, 2004", 32 pgs.

"U.S. Appl. No. 09/940,273, Response filed Nov. 28, 2005 to Non Final Office Action mailed Oct. 17, 2005", 17 pgs.

"U.S. Appl. No. 09/940,377, Non Final Office Action mailed May 4, 2004", 10 pgs.

"U.S. Appl. No. 09/940,377, Non Final Office Action mailed Dec. 17, 2003", 14 pgs.

"U.S. Appl. No. 09/940,377, Response filed Mar. 17, 2004 to Non Final Office Action mailed Dec. 17, 2003", 36 pgs.

"U.S. Appl. No. 09/940,377, Response filed Jul. 13, 2004 to Non Final Office Action mailed May 4, 2004", 20 pgs.

"U.S. Appl. No. 09/940,378, Final Office Action mailed Mar. 23, 2004", 7 pgs.

"U.S. Appl. No. 09/940,378, Final Office Action mailed Jun. 22, 2005", 8 pgs.

"U.S. Appl. No. 09/940,378, Non Final Office Action mailed Jan. 13, 2005", 9 pgs.

"U.S. Appl. No. 09/940,378, Non Final Office Action mailed Feb. 22, 2006", 6 pgs.

"U.S. Appl. No. 09/940,378, Non Final Office Action mailed Jul. 1, 2004", 10 pgs.

"U.S. Appl. No. 09/940,378, Non Final Office Action mailed Sep. 1, 2005", 7 pgs.

"U.S. Appl. No. 09/940,378, Non Final Office Action mailed Oct. 7, 2003", 17 pgs.

"U.S. Appl. No. 09/940,378, Response filed Feb. 6, 2004 to Non Final Office Action mailed Oct. 7, 2003", 6 pgs.

"U.S. Appl. No. 09/940,378, Response filed May 13, 2005 to Non Final Office Action mailed Jan. 13, 2005", 9 pgs.

"U.S. Appl. No. 09/940,378, Response filed May 17, 2006 to Non Final Office Action mailed Feb. 22, 2006", 8 pgs.

"U.S. Appl. No. 09/940,378, Response filed May 19, 2004 to Final Office Action mailed Mar. 23, 2004", 12 pgs.

"U.S. Appl. No. 09/940,378, Response filed Aug. 17, 2005 to Final Office Action mailed Jun. 22, 2005", 7 pgs.

"U.S. Appl. No. 09/940,378, Response filed Sep. 30, 2004 to Non Final Office Action mailed Jul. 1, 2004", 8 pgs.

"U.S. Appl. No. 09/940,378, Response filed Nov. 17, 2005 to Non Final Office Action mailed Sep. 1, 2005", 8 pgs.

"U.S. Appl. No. 09/940,471, Final Office Action mailed Mar. 24, 2004", 12 pgs.

"U.S. Appl. No. 09/940,471, Final Office Action mailed Jul. 11, 2005", 8 pgs.

"U.S. Appl. No. 09/940,471, Non Final Office Action mailed Jan. 13, 2005", 8 pgs.

(56) References Cited

OTHER PUBLICATIONS

"U.S. Appl. No. 09/940,471, Non Final Office Action mailed Jul. 14, 2004", 7 pgs.
"U.S. Appl. No. 09/940,471, Non Final Office Action mailed Sep. 1, 2005", 9 pgs.
"U.S. Appl. No. 09/940,471, Non Final Office Action mailed Oct. 8, 2003", 12 pgs.
"U.S. Appl. No. 09/940,471, Response filed Feb. 6, 2004 to Non Final Office Action mailed Oct. 8, 2003", 7 pgs.
"U.S. Appl. No. 09/940,471, Response filed Apr. 25, 2005 to Final Office Action mailed Jan. 13, 2005", 18 pgs.
"U.S. Appl. No. 09/940,471, Response filed May 21, 2004 to Final Office Action mailed Mar. 24, 2004", 17 pgs.
"U.S. Appl. No. 09/940,471, Response filed Aug. 22, 2005 to Final Office Action mailed Jul. 11, 2005", 7 pgs.
"U.S. Appl. No. 09/940,471, Response filed Oct. 14, 2004 to Non Final Office Action mailed Jul. 14, 2004", 11 pgs.
"U.S. Appl. No. 09/940,471, Response filed Nov. 17, 2005 to Non Final Office Action mailed Sep. 1, 2005", 9 pgs.
"U.S. Appl. No. 10/011,506, Final Office Action mailed Sep. 28, 2004", 5 pgs.
"U.S. Appl. No. 10/011,506, Non Final Office Action mailed Mar. 15, 2004", 20 pgs.
"U.S. Appl. No. 10/011,506, Response filed Jun. 15, 2004 to Non Final Office Action mailed Mar. 15, 2004", 16 pgs.
"U.S. Appl. No. 10/011,533, Final Office Action mailed Sep. 28, 2004", 4 pgs.
"U.S. Appl. No. 10/011,533, Non Final Office Action mailed Mar. 4, 2004", 9 pgs.
"U.S. Appl. No. 10/011,533, Response filed Jun. 2, 2004 to Non Final Office Action mailed Mar. 4, 2004", 11 pgs.
"U.S. Appl. No. 10/011,533, Response filed Sep. 23, 2004 to Non Final Office Action mailed Mar. 4, 2004", 3 pgs.
"U.S. Appl. No. 10/011,566, Final Office Action mailed Apr. 5, 2005", 7 pgs.
"U.S. Appl. No. 10/011,566, Non Final Office Action mailed Apr. 7, 2004", 8 pgs.
"U.S. Appl. No. 10/011,566, Non Final Office Action mailed Oct. 13, 2004", 8 pgs.
"U.S. Appl. No. 10/011,566, Response filed Jan. 13, 2005 to Non Final Office Action mailed Oct. 13, 2004", 11 pgs.
"U.S. Appl. No. 10/011,566, Response filed Jun. 6, 2005 to Final Office Action mailed Apr. 5, 2005", 9 pgs.
"U.S. Appl. No. 10/011,566, Response filed Jun. 29, 2004 to Non Final Office Action mailed Apr. 7, 2004", 17 pgs.
"U.S. Appl. No. 10/011,860, Final Office Action mailed Mar. 9, 2005", 9 pgs.
"U.S. Appl. No. 10/011,860, Non Final Office Action mailed Mar. 4, 2004", 13 pgs.
"U.S. Appl. No. 10/011,860, Non Final Office Action mailed Jun. 1, 2005", 8 pgs.
"U.S. Appl. No. 10/011,860, Non Final Office Action mailed Sep. 22, 2004", 9 pgs.
"U.S. Appl. No. 10/011,860, Non Final Office Action mailed Nov. 1, 2005", 11 pgs.
"U.S. Appl. No. 10/011,860, Response filed Feb. 1, 2006 to Non Final Office Action mailed Nov. 1, 2005", 12 pgs.
"U.S. Appl. No. 10/011,860, Response filed May 6, 2005 to Final Office Action mailed Mar. 9, 2005", 8 pgs.
"U.S. Appl. No. 10/011,860, Response filed Jun. 3, 2004 to Non Final Office Action mailed Mar. 4, 2004", 31 pgs.
"U.S. Appl. No. 10/011,860, Response filed Aug. 17, 2005 to Non Final Office Action mailed Jun. 1, 2005", 11 pgs.
"U.S. Appl. No. 10/011,860, Response filed Dec. 17, 2004 to Non Final Office Action mailed Sep. 22, 2004", 20 pgs.
"U.S. Appl. No. 10/011,947, Amendment filed Jul. 29, 2004", 3 pgs.
"U.S. Appl. No. 10/011,947, Final Office Action mailed May 4, 2005", 8 pgs.
"U.S. Appl. No. 10/011,947, Non Final Office Action mailed Apr. 8, 2004", 11 pgs.
"U.S. Appl. No. 10/011,947, Non Final Office Action mailed Jun. 28, 2005", 7 pgs.
"U.S. Appl. No. 10/011,947, Response filed Jun. 14, 2005 to Final Office Action mailed May 4, 2005", 7 pgs.
"U.S. Appl. No. 10/011,947, Response filed Jul. 8, 2004 to Non Final Office Action mailed Apr. 8, 2004", 24 pgs.
"U.S. Appl. No. 10/011,947, Response filed Sep. 20, 2005 to Non Final Office Action mailed Jun. 28, 2005", 9 pgs.
"U.S. Appl. No. 10/011,958, Final Office Action mailed Sep. 22, 2004", 5 pgs.
"U.S. Appl. No. 10/011,958, Non Final Office Action mailed Mar. 4, 2004", 14 pgs.
"U.S. Appl. No. 10/011,958, Response filed Jun. 2, 2004 to Non Final Office Action mailed Mar. 4, 2004", 14 pgs.
"U.S. Appl. No. 10/013,980, Advisory Action mailed Jan. 27, 2005", 2 pgs.
"U.S. Appl. No. 10/013,980, Final Office Action mailed Oct. 26, 2005", 7 pgs.
"U.S. Appl. No. 10/013,980, Final Office Action mailed Nov. 16, 2004", 10 pgs.
"U.S. Appl. No. 10/013,980, Non Final Office Action mailed Apr. 25, 2005", 7 pgs.
"U.S. Appl. No. 10/013,980, Non Final Office Action mailed May 5, 2004", 9 pgs.
"U.S. Appl. No. 10/013,980, Response filed Jan. 14, 2005 to Final Office Action mailed Nov. 16, 2004", 13 pgs.
"U.S. Appl. No. 10/013,980, Response filed Feb. 18, 2005 to Final Office Action mailed Nov. 16, 2004", 12 pgs.
"U.S. Appl. No. 10/013,980, Response filed Jul. 29, 2005 to Non Final Office Action mailed Apr. 25, 2005", 13 pgs.
"U.S. Appl. No. 10/013,980, Response filed Aug. 5, 2004 to Non Final Office Action mailed May 5, 2004", 9 pgs.
"U.S. Appl. No. 10/013,980, Response filed Sep. 24, 2004 to Non Final Office Action mailed May 5, 2004", 3 pgs.
"U.S. Appl. No. 10/013,980, Response filed Dec. 22, 2005 to Final Office Action mailed Oct. 26, 2005", 6 pgs.
"U.S. Appl. No. 10/015,202, Final Office Action mailed Jul. 26, 2004", 11 pgs.
"U.S. Appl. No. 10/015,202, Non Final Office Action mailed Mar. 9, 2004", 21 pgs.
"U.S. Appl. No. 10/015,202, Non Final Office Action mailed Oct. 19, 2004", 7 pgs.
"U.S. Appl. No. 10/015,202, Response filed Jan. 19, 2005 to Non Final Office Action mailed Oct. 19, 2004", 6 pgs.
"U.S. Appl. No. 10/015,202, Response filed Jun. 2, 2004 to Non Final Office Action mailed Mar. 9, 2004", 15 pgs.
"U.S. Appl. No. 10/015,202, Response filed Sep. 21, 2004 to Final Office Action mailed Jul. 26, 2004", 9 pgs.
"U.S. Appl. No. 10/124,159, Advisory Action mailed Oct. 13, 2006", 3 pgs.
"U.S. Appl. No. 10/124,159, Final Office Action mailed Aug. 8, 2006", 14 pgs.
"U.S. Appl. No. 10/124,159, Non Final Office Action mailed Feb. 15, 2006", 15 pgs.
"U.S. Appl. No. 10/124,159, Non Final Office Action mailed Mar. 24, 2005", 9 pgs.
"U.S. Appl. No. 10/124,159, Non Final Office Action mailed Sep. 6, 2005", 13 pgs.
"U.S. Appl. No. 10/124,159, Response filed May 15, 2006 to Non Final Office Action mailed Feb. 15, 2006", 20 pgs.
"U.S. Appl. No. 10/124,159, Response filed Jun. 24, 2005 to Non Final Office Action mailed Mar. 24, 2005", 15 pgs.
"U.S. Appl. No. 10/124,159, Response filed Sep. 29, 2006 to Final Office Action mailed Aug. 8, 2006", 17 pgs.
"U.S. Appl. No. 10/124,159, Response filed Nov. 1, 2006 to Advisory Action mailed Oct. 13, 2006", 4 pgs.
"U.S. Appl. No. 10/150,434, Advisory Action mailed Nov. 15, 2005", 3 pgs.
"U.S. Appl. No. 10/150,434, Final Office Action mailed Sep. 16, 2005", 8 pgs.
"U.S. Appl. No. 10/150,434, Non Final Office Action mailed Feb. 23, 2005", 8 pgs.

(56) References Cited

OTHER PUBLICATIONS

"U.S. Appl. No. 10/150,434, Non Final Office Action mailed Mar. 8, 2006", 9 pgs.

"U.S. Appl. No. 10/150,434, Response filed May 31, 2006 to Non Final Office Action mailed Mar. 8, 2006", 13 pgs.

"U.S. Appl. No. 10/150,434, Response filed Jun. 23, 2005 to Non Final Office Action mailed Feb. 23, 2005", 12 pgs.

"U.S. Appl. No. 10/150,434, Response filed Nov. 3, 2005 to Final Office Action mailed Sep. 16, 2005", 13 pgs.

"U.S. Appl. No. 10/150,434, Response filed Dec. 15, 2005 to Final Office Action mailed Sep. 16, 2005", 13 pgs.

"U.S. Appl. No. 10/870,278, Response filed Jun. 28, 2007 to Non Final Office Action mailed Feb. 2, 2007", 11 pgs.

"U.S. Appl. No. 10/968,889, Application filed Dec. 21, 2004", 38 pgs.

"U.S. Appl. No. 10/968,889, Examiner Interview Summary mailed Mar. 22, 2010", 3 pgs.

"U.S. Appl. No. 10/968,889, Examiner Interview Summary mailed Apr. 14, 2009", 2 pgs.

"U.S. Appl. No. 10/968,889, Examiner Interview Summary mailed Apr. 16, 2009", 2 pgs.

"U.S. Appl. No. 10/968,889, Examiner Interview Summary mailed May 28, 2008", 2 pgs.

"U.S. Appl. No. 10/968,889, Final Office Action Jul. 9, 2013", 25 pgs.

"U.S. Appl. No. 10/968,889, Final Office Action mailed Jul. 13, 2010", 18 pgs.

"U.S. Appl. No. 10/968,889, Non Final Office Action mailed Apr. 17, 2009", 13 pgs.

"U.S. Appl. No. 10/968,889, Non Final Office Action mailed Oct. 17, 2008", 14 pgs.

"U.S. Appl. No. 10/968,889, Non-Final Office Action mailed Dec. 5, 2012", 19 pgs.

"U.S. Appl. No. 10/968,889, Response filed Apr. 28, 2010 to Restriction Requirement mailed Dec. 30, 2009", 5 pgs.

"U.S. Appl. No. 10/968,889, Response filed Jun. 5, 2008 to Restriction Requirement mailed Dec. 6, 2007", 3 pgs.

"U.S. Appl. No. 10/968,889, Response filed Jun. 5, 2013 to Non-Final Office Action mailed Dec. 5, 2012", 63 pgs.

"U.S. Appl. No. 10/968,889, Response filed Jul. 13, 2010 to Final Office Action mailed Apr. 11, 2011", 59 pgs.

"U.S. Appl. No. 10/968,889, Response filed Oct. 19, 2009 to Non Final Office Action mailed Apr. 17, 2009", 58 pgs.

"U.S. Appl. No. 10/968,889, Restriction Requirement mailed Dec. 6, 2007", 6 pgs.

"U.S. Appl. No. 10/968,889, Restriction Requirement mailed Dec. 30, 2009", 11 pgs.

"U.S. Appl. No. 10/968,889, Supplemental Amendment filed Mar. 8, 2005", 21 pgs.

"U.S. Appl. No. 10/968,889, Supplemental Preliminary Amendment filed Apr. 11, 2005", 33 pgs.

"U.S. Appl. No. 10/968,889, Supplemental Preliminary Amendment filed Nov. 10, 2004", 18 pgs.

"U.S. Appl. No. 10/984,392, Non Final Office Action mailed May 16, 2006", 9 pgs.

"U.S. Appl. No. 10/984,392, Response filed Aug. 1, 2006 to Non Final Office Action mailed May 16, 2006", 8 pgs.

"U.S. Appl. No. 10/984,585, Non Final Office Action mailed Mar. 14, 2007", 15 pgs.

"U.S. Appl. No. 10/984,585, Non Final Office Action mailed May 30, 2008", 10 pgs.

"U.S. Appl. No. 10/984,585, Non Final Office Action mailed Nov. 19, 2007", 9 pgs.

"U.S. Appl. No. 10/984,585, Response filed Feb. 18, 2008 to Non Final Office Action mailed Nov. 19, 2007", 9 pgs.

"U.S. Appl. No. 10/984,585, Response filed Jun. 12, 2007 to Non Final Office Action mailed Mar. 14, 2007", 12 pgs.

"U.S. Appl. No. 10/984,585, Response filed Sep. 30, 2008 to Non Final Office Action mailed May 30, 2008", 7 pgs.

"U.S. Appl. No. 11/040,912, Advisory Action mailed Jul. 9, 2007", 2 pgs.

"U.S. Appl. No. 11/040,912, Final Office Action mailed May 18, 2007", 8 pgs.

"U.S. Appl. No. 11/040,912, Non Final Office Action mailed Jan. 5, 2007", 8 pgs.

"U.S. Appl. No. 11/040,912, Non Final Office Action mailed Mar. 25, 2008", 8 pgs.

"U.S. Appl. No. 11/040,912, Non Final Office Action mailed Sep. 28, 2007", 10 pgs.

"U.S. Appl. No. 11/040,912, Response filed Mar. 5, 2007 to Non Final Office Action mailed Jan. 5, 2007", 9 pgs.

"U.S. Appl. No. 11/040,912, Response filed Jun. 23, 2008 to Non Final Office Action mailed Mar. 25, 2008", 5 pgs.

"U.S. Appl. No. 11/040,912, Response filed Jun. 26, 2007 to Final Office Action mailed May 18, 2007", 8 pgs.

"U.S. Appl. No. 11/040,912, Response filed Dec. 27, 2007 to Non Final Office Action mailed Sep. 28, 2007", 8 pgs.

"U.S. Appl. No. 11/060,869, Final Office Action mailed Sep. 11, 2007", 7 pgs.

"U.S. Appl. No. 11/060,869, Non Final Office Action mailed Mar. 19, 2007", 13 pgs.

"U.S. Appl. No. 11/060,869, Non Final Office Action mailed May 23, 2008", 10 pgs.

"U.S. Appl. No. 11/060,869, Response filed Jun. 1, 2007 to Non Final Office Action mailed Mar. 19, 2007", 13 pgs.

"U.S. Appl. No. 11/060,869, Response filed Aug. 22, 2008 to Non Final Office Action mailed May 23, 2008", 11 pgs.

"U.S. Appl. No. 11/060,869, Response filed Oct. 30, 2007 to Final Office Action mailed Sep. 11, 2007", 8 pgs.

"U.S. Appl. No. 11/205,447, Advisory Action mailed Sep. 24, 2012", 3 pgs.

"U.S. Appl. No. 11/205,447, Final Office Action mailed Feb. 2, 2012", 6 pgs.

"U.S. Appl. No. 11/205,447, Final Office Action mailed Jun. 23, 2009", 12 pgs.

"U.S. Appl. No. 11/205,447, Final Office Action mailed Jul. 12, 2012", 9 pgs.

"U.S. Appl. No. 11/205,447, Final Office Action mailed Nov. 26, 2010", 8 pgs.

"U.S. Appl. No. 11/205,447, Non Final Office Action mailed Jan. 16, 2008", 12 pgs.

"U.S. Appl. No. 11/205,447, Non Final Office Action mailed Mar. 21, 2012", 8 pgs.

"U.S. Appl. No. 11/205,447, Non Final Office Action mailed Sep. 16, 2009", 8 pgs.

"U.S. Appl. No. 11/205,447, Non Final Office Action mailed Sep. 21, 2011", 7 pgs.

"U.S. Appl. No. 11/205,447, Non Final Office Action mailed Dec. 24, 2008", 12 pgs.

"U.S. Appl. No. 11/205,447, Response filed Feb. 28, 2011 to Final Office Action mailed Nov. 26, 2010", 10 pgs.

"U.S. Appl. No. 11/205,447, Response filed Feb. 29, 2012 to Final Office Action mailed Feb. 2, 2012", 5 pgs.

"U.S. Appl. No. 11/205,447, Response filed Mar. 23, 2009 to Non Final Office Action mailed Dec. 24, 2008", 9 pgs.

"U.S. Appl. No. 11/205,447, Response filed Apr. 16, 2008 to Non Final Office Action mailed Jan. 16, 2008", 13 pgs.

"U.S. Appl. No. 11/205,447, Response filed Jun. 19, 2012 to Non Final Office Action mailed Mar. 21, 2012", 10 pgs.

"U.S. Appl. No. 11/205,447, Response filed Aug. 24, 2009 to Final Office Action mailed Jun. 23, 2009", 8 pgs.

"U.S. Appl. No. 11/205,447, Response filed Sep. 12, 2012 to Final Office Action mailed Jul. 12, 2012", 15 pgs.

"U.S. Appl. No. 11/205,447, Response filed Nov. 12, 2012 to Advisory Action mailed Sep. 24, 2012", 16 pgs.

"U.S. Appl. No. 11/205,447, Response filed Dec. 15, 2009 to Non Final Office Action mailed Sep. 16, 2009", 9 pgs.

"U.S. Appl. No. 11/205,447, Response filed Dec. 15, 2011 to Non Final Office Action mailed Sep. 21, 2011", 6 pgs.

"U.S. Appl. No. 11/250,680, Final Office Action mailed Sep. 14, 2007", 9 pgs.

(56) References Cited

OTHER PUBLICATIONS

"U.S. Appl. No. 11/250,680, Non Final Office Action mailed Apr. 11, 2007", 7 pgs.

"U.S. Appl. No. 11/250,680, Response filed Jun. 18, 2007 to Non Final Office Action mailed Apr. 11, 2007", 10 pgs.

"U.S. Appl. No. 11/250,680, Response filed Nov. 8, 2007 to Final Office Action mailed Sep. 14, 2007", 8 pgs.

"U.S. Appl. No. 11/349,326, Advisory Action mailed Jan. 13, 2009", 4 pgs.

"U.S. Appl. No. 11/349,326, Final Office Action mailed Jan. 22, 2010", 8 pgs.

"U.S. Appl. No. 11/349,326, Final Office Action mailed Oct. 24, 2008", 12 pgs.

"U.S. Appl. No. 11/349,326, Non Final Office Action mailed May 5, 2009", 8 pgs.

"U.S. Appl. No. 11/349,326, Non Final Office Action mailed May 13, 2008", 13 pgs.

"U.S. Appl. No. 11/349,326, Response filed Feb. 24, 2009 to Advisory Action mailed Jan. 13, 2009", 4 pgs.

"U.S. Appl. No. 11/349,326, Response filed Apr. 22, 2010 to Final Office Action mailed Jan. 22, 2010", 6 pgs.

"U.S. Appl. No. 11/349,326, Response filed Aug. 5, 2009 to Non Final Office Action mailed May 5, 2009", 10 pgs.

"U.S. Appl. No. 11/349,326, Response filed Aug. 13, 2008 to Non Final Office Action mailed May 13, 2008", 7 pgs.

"U.S. Appl. No. 11/349,326, Response filed Dec. 24, 2008 to Final Office Action mailed Oct. 24, 2008", 8 pgs.

"U.S. Appl. No. 11/429,089, Non Final Office Action mailed Mar. 6, 2009", 7 pgs.

"U.S. Appl. No. 11/429,089, Non Final Office Action mailed Sep. 12, 2008", 7 pgs.

"U.S. Appl. No. 11/429,089, Response filed Jun. 8, 2009 to Non Final Office Action mailed Mar. 6, 2009", 5 pgs.

"U.S. Appl. No. 11/429,089, Response filed Dec. 12, 2008 to Non Final Office Action mailed Sep. 12, 2008", 7 pgs.

"U.S. Appl. No. 11/447,531, Advisory Action mailed Mar. 20, 2009", 3 pgs.

"U.S. Appl. No. 11/447,531, Final Office Action mailed Jan. 2, 2009", 8 pgs.

"U.S. Appl. No. 11/447,531, Non Final Office Action mailed Apr. 27, 2009", 5 pgs.

"U.S. Appl. No. 11/447,531, Non Final Office Action mailed Jul. 11, 2008", 11 pgs.

"U.S. Appl. No. 11/447,531, Response filed Mar. 2, 2009 to Final Office Action mailed Jan. 2, 2009", 9 pgs.

"U.S. Appl. No. 11/447,531, Response filed Apr. 2, 2009 to Advisory Action mailed Mar. 20, 2009", 10 pgs.

"U.S. Appl. No. 11/447,531, Response filed Jul. 24, 2009 to Non Final Office Action mailed Apr. 27, 2008", 3 pgs.

"U.S. Appl. No. 11/447,531, Response filed Oct. 10, 2008 to Non Final Office Action mailed Jul. 11, 2008", 13 pgs.

"U.S. Appl. No. 11/451,241, Non Final Office Action mailed Mar. 31, 2009", 7 pgs.

"U.S. Appl. No. 11/451,241, Response filed Apr. 15, 2009 to Non Final Office Action mailed Mar. 31, 2009", 11 pgs.

"U.S. Appl. No. 11/553,785, Final Office Action mailed Aug. 19, 2009", 11 pgs.

"U.S. Appl. No. 11/553,785, Non Final Office Action mailed Mar. 9, 2009", 7 pgs.

"U.S. Appl. No. 11/553,785, Response filed Jun. 9, 2009 to Non Final Office Action mailed Mar. 9, 2009", 10 pgs.

"U.S. Appl. No. 11/553,785, Response filed Nov. 19, 2009 to Final Office Action mailed Aug. 19, 2009", 12 pgs.

"U.S. Appl. No. 11/554,185, Advisory Action mailed Jan. 25, 2010", 3 pgs.

"U.S. Appl. No. 11/554,185, Examiner Interview Summary mailed Sep. 10, 2013", 3 pgs.

"U.S. Appl. No. 11/554,185, Final Office Action mailed Jun. 14, 2013", 11 pgs.

"U.S. Appl. No. 11/554,185, Final Office Action mailed Oct. 15, 2009", 9 pgs.

"U.S. Appl. No. 11/554,185, Non Final Office Action mailed Mar. 19, 2009", 11 pgs.

"U.S. Appl. No. 11/554,185, Non Final Office Action mailed Dec. 3, 2012", 10 pgs.

"U.S. Appl. No. 11/554,185, Response filed Feb. 25, 2010 to Advisory Action mailed Jan. 25, 2010", 10 pgs.

"U.S. Appl. No. 11/554,185, Response filed Mar. 1, 2013 to Non Final Office Action mailed Dec. 3, 2012", 9 pgs.

"U.S. Appl. No. 11/554,185, Response filed Jun. 19, 2009 to Non Final Office Action mailed Mar. 19, 2009", 10 pgs.

"U.S. Appl. No. 11/554,185, Response filed Sep. 6, 2013 to Final Office Action mailed Jun. 14, 2013", 7 pgs.

"U.S. Appl. No. 11/554,185, Response filed Dec. 15, 2009 to Final Office Action mailed Oct. 15, 2009", 8 pgs.

"U.S. Appl. No. 11/555,424, 312 Amendment filed Jun. 2, 2010", 5 pgs.

"U.S. Appl. No. 11/555,424, Non Final Office Action mailed Apr. 6, 2009", 8 pgs.

"U.S. Appl. No. 11/555,424, Non Final Office Action mailed Sep. 16, 2009", 9 pgs.

"U.S. Appl. No. 11/555,424, Response filed Jul. 2, 2009 to Non Final Office Action mailed Apr. 6, 2009", 11 pgs.

"U.S. Appl. No. 11/555,424, Response filed Dec. 16, 2009 to Non Final Office Action mailed Sep. 16, 2009", 5 pgs.

"U.S. Appl. No. 11/555,436, Non Final Office Action mailed Jun. 28, 2007", 7 pgs.

"U.S. Appl. No. 11/555,436, Response filed Sep. 28, 2007 to Non Final Office Action mailed Jun. 28, 2007", 14 pgs.

"U.S. Appl. No. 11/555,447, Non Final Office Action mailed Apr. 8, 2009", 7 pgs.

"U.S. Appl. No. 11/555,447, Non Final Office Action mailed Sep. 25, 2009", 10 pgs.

"U.S. Appl. No. 11/555,447, Response filed Jul. 8, 2009 to Non Final Office Action mailed Apr. 8, 2009", 7 pgs.

"U.S. Appl. No. 11/555,447, Response filed Dec. 28, 2009 to Non Final Office Action mailed Sep. 25, 2009", 8 pgs.

"U.S. Appl. No. 11/555,459, Non Final Office Action mailed Apr. 9, 2009", 9 pgs.

"U.S. Appl. No. 11/555,459, Non Final Office Action mailed Sep. 29, 2009", 13 pgs.

"U.S. Appl. No. 11/555,459, Response filed Jul. 8, 2009 to Non Final Office Action mailed Apr. 9, 2009", 13 pgs.

"U.S. Appl. No. 11/555,459, Response filed Dec. 29, 2009 to Non Final Office Action mailed Sep. 29, 2009", 12 pgs.

"U.S. Appl. No. 11/680,107, Advisory Action mailed Jul. 2, 2010", 3 pgs.

"U.S. Appl. No. 11/680,107, Final Office Action mailed Apr. 16, 2010", 8 pgs.

"U.S. Appl. No. 11/680,107, Final Office Action mailed Jul. 16, 2012", 9 pgs.

"U.S. Appl. No. 11/680,107, Non Final Office Action mailed Mar. 26, 2012", 8 pgs.

"U.S. Appl. No. 11/680,107, Non Final Office Action mailed Sep. 17, 2009", 11 pgs.

"U.S. Appl. No. 11/680,107, Non Final Office Action mailed Sep. 25, 2012", 6 pgs.

"U.S. Appl. No. 11/680,107, Response filed Jun. 16, 2010 to Final Office Action mailed Apr. 16, 2010", 7 pgs.

"U.S. Appl. No. 11/680,107, Response filed Jun. 25, 2012 to Non Final Office Action mailed Mar. 26, 2012", 10 pgs.

"U.S. Appl. No. 11/680,107, Response filed Jul. 16, 2010 to Advisory Action mailed Jul. 2, 2010", 6 pgs.

"U.S. Appl. No. 11/680,107, Response filed Sep. 14, 2012 to Final Office Action mailed Jul. 16, 2012", 9 pgs.

"U.S. Appl. No. 11/680,107, Response filed Dec. 16, 2009 to Non Final Office Action mailed Sep. 17, 2009", 9 pgs.

"U.S. Appl. No. 11/680,107, Response filed Dec. 20, 2012 to Non Final Office Action mailed Sep. 25, 2012", 7 pgs.

"U.S. Appl. No. 11/877,323, Non Final Office Action mailed Mar. 5, 2010", 8 pgs.

"U.S. Appl. No. 11/877,323, Non Final Office Action mailed Sep. 1, 2010", 9 pgs.

"U.S. Appl. No. 11/877,323, Response filed Jun. 7, 2010 to Non Final Office Action mailed Mar. 5, 2010", 8 pgs.

(56) References Cited

OTHER PUBLICATIONS

"U.S. Appl. No. 11/877,323, Response filed Nov. 30, 2010 to Non Final Office Action mailed Sep. 1, 2010", 8 pgs.
"U.S. Appl. No. 11/981,140, Final Office Action mailed Apr. 22, 2011", 17 pgs.
"U.S. Appl. No. 11/981,140, Non-Final Office Action mailed Dec. 7, 2012", 12 pgs.
"U.S. Appl. No. 11/981,140, Preliminary Amendment filed Feb. 15, 2008", 23 pgs.
"U.S. Appl. No. 11/981,140, Response filed May 21, 2012 to Final Office Action mailed Apr. 22, 2011", 7 pgs.
"U.S. Appl. No. 11/981,410, Application filed Oct. 31, 2007", 63 pgs.
"U.S. Appl. No. 11/981,410, Non Final Office Action mailed Aug. 23, 2010", 15 pgs.
"U.S. Appl. No. 11/981,410, Preliminary Amendment filed Feb. 12, 2008", 3 pgs.
"U.S. Appl. No. 11/981,410, Response filed Feb. 22, 2011 to Non Final Office Action mailed Aug. 23, 2010", 45 pgs.
"U.S. Appl. No. 12/698,609, Non Final Office Action mailed Feb. 21, 2012", 8 pgs.
"U.S. Appl. No. 12/698,609, Response filed May 21, 2012 to Non Final Office Action mailed Feb. 21, 2012", 7 pgs.
"U.S. Appl. No. 13/429,777, Examiner Interview Summary mailed Jun. 6, 2012", 1 pg.
"U.S. Appl. No. 13/429,777, Non Final Office Action mailed Jun. 6, 2012", 9 pgs.
"U.S. Appl. No. 13/429,777, Response filed Sep. 6, 2012 to Non Final Office Action mailed Jun. 6, 2012", 8 pgs.
"U.S. Appl. No. 13/436,417, Non Final Office Action mailed Aug. 23, 2013", 5 pgs.
"U.S. Appl. No. 13/765,088 , Response filed Aug. 23, 2013 to Non Final Office Action mailed May 23, 2013", 8 pgs.
"U.S. Appl. No. 13/765,088, Non Final Office Action mailed May 23, 2013", 5 pgs.
"U.S. Appl. No. 13/785,894, Non Final Office Action mailed Apr. 30, 2013", 9 pgs.
"U.S. Appl. No. 13/785,894, Response filed Aug. 30, 2013 to Non Final Office Action mailed Apr. 30, 2013", 10 pgs.
"U.S. Appl. No. 13/887,652, Non-Final Office Action mailed Aug. 14, 2013", 7 pgs.
"U.S. Appl. No. 60/252,811, filed Nov. 22, 2000", 19 pgs.
"U.S. Appl. No. 60/272,962, filed Feb. 28, 2001", 6 pgs.
"European Application Serial No. 01971141.5, Office Action mailed May 2, 2013", 2 pgs.
"European Application Serial No. 01973151.2, Office Action mailed Jan. 20, 2011", 5 pgs.
"European Application Serial No. 01973151.2, Office Action mailed Aug. 28, 2006", 4 pgs.
"European Application Serial No. 01973151.2, Response filed May 19, 2011 to Office Action mailed Jan. 20, 2011", 16 pgs.
"European Application Serial No. 01973151.2, Response filed Dec. 20, 2006 to Office Action mailed Aug. 28, 2006", 22 pgs.
"European Application Serial No. 019731512, Summons to Attend Oral Proceedings mailed Oct. 11, 2013", 6 pgs.
"European Application Serial No. 02785702.8, Office Action mailed Jul. 31, 2009", 5 pgs.
"European Application Serial No. 02785702.8, Office Action mailed Aug. 8, 2012", 5 pgs.
"European Application Serial No. 02785702.8, Office Action mailed Dec. 7, 2012", 5 pgs.
"European Application Serial No. 02785702.8, Response filed Dec. 8, 2009 to Office Action mailed Jul. 31, 2009", 5 pgs.
"International Application Serial No. PCT/IB2002/003469, International Preliminary Examination Report mailed Sep. 2, 2003", 5 pgs.
"International Application Serial No. PCT/IB2002/003469, International Search Report mailed Feb. 14, 2003", 4 pgs.
"International Application Serial No. PCT/IB2002/003469, Written Opinion mailed May 12,2003", 5 pgs.
"International Application Serial No. PCT/IB2002/003484, International Preliminary Examination Report mailed Sep. 2, 2003", 5 pgs.
"International Application Serial No. PCT/IB2002/003484, International Search Report mailed Feb. 14, 2003", 5 pgs.
"International Application Serial No. PCT/IB2002/003484, Written Opinion mailed May 12, 2003", 5 pgs.
"International Application Serial No. PCT/IB2002/003503, International Preliminary Examination Report mailed Sep. 2, 2003", 5 pgs.
"International Application Serial No. PCT/IB2002/003503, International Search Report mailed Feb. 18, 2003", 4 pgs.
"International Application Serial No. PCT/IB2002/003503, Written Opinion mailed May 12, 2003", 5 pgs.
"International Application Serial No. PCT/IB2002/003522, International Preliminary Examination Report mailed Sep. 2, 2003", 5 pgs.
"International Application Serial No. PCT/IB2002/003522, International Search Report mailed Feb. 14, 2003", 4 pgs.
"International Application Serial No. PCT/IB2002/003522, Written Opinion mailed May 12, 2003", 6 pgs.
"International Application Serial No. PCT/IB2002/004475, International Search Report mailed Apr. 25, 2003", 4 pgs.
"International Application Serial No. PCT/IB2002/004490, International Search Report mailed Apr. 16, 2003", 3 pgs.
"International Application Serial No. PCT/IB2002/004498, International Search Report mailed Apr. 16, 2003", 8 pgs.
"International Application Serial No. PCT/IB2002/004507, International Search Report mailed Apr. 16, 2003", 4 pgs.
"International Application Serial No. PCT/IB2002/004516, International Search Report mailed Apr. 16, 2003", 4 pgs.
"International Application Serial No. PCT/IB2003/004498, International Search Report mailed Apr. 16, 2003", 2 pgs.
"International Application Serial No. PCT/IB2003/004543, International Search Report mailed Apr. 16, 2003", 4 pgs.
"International Application Serial No. PCT/US2001/029106, International Preliminary Examination Report mailed Dec. 17, 2002", 6 pgs.
"International Application Serial No. PCT/US2001/029106, International Search Report mailed Mar. 21, 2002", 4 pgs.
"International Application Serial No. PCT/US2001/029106, Written Opinion mailed Sep. 3, 2002", 6 pgs.
"International Application Serial No. PCT/US2001/029168, International Search Report mailed Mar. 26, 2002", 5 pgs.
"International Application Serial No. PCT/US2001/029168, Written Opinion mailed Sep. 10, 2002", 7 pgs.
"International Application Serial No. PCT/US2003/010666, International Search Report mailed Oct. 1, 2003", 1 pg.
Krahn, et al., "Maturation of the Sensed Electrogram Amplitude Over Time in a New Subcutaneous Implantable Loop Recorder", PACE; vol. 20, Issue 6, (Jun. 1997), 1686-1690.
Zellerhoff, et al., "How Can We Identity the Best Implantation Site for an ECG Event Recorder?", PACE; vol. 23, Issue 10, (Oct. 2000), 1545-1549.
U.S. Appl. No. 11/554,185, Final Office Action mailed Sep. 30, 2013, 8 pgs.
U.S. Appl. No. 11/554,185, Non Final Office Action mailed Feb. 28, 2014, 10 pgs.
U.S. Appl. No. 11/554,185, Response filed Dec. 20, 2013 to Final Office Action mailed Sep. 20, 2013, 15 pgs.
U.S. Appl. No. 13/785,894, Advisory Action mailed Nov. 22, 2013, 2 pgs.
U.S. Appl. No. 13/785,894, Final Office Action mailed Sep. 16, 2013, 8 pgs.
U.S. Appl. No. 13/785,894, Non Final Office Action mailed Dec. 30, 2013, 8 pgs.
U.S. Appl. No. 13/785,894, Response filed Nov. 18, 2013 to Final Office Action mailed Sep. 16, 2013, 8 pgs.
U.S. Appl. No. 13/785,894, Response filed Dec. 16, 2013 to Final Office Action mailed Sep. 16, 2013, 8 pgs.
European Application Serial No. 01973151.2, Communication under Rule 71(3) EPC mailed Mar. 3, 2014, 9 pgs.
Bocker, D., et al., "Treatment with implantable defibrillators in childhood", Herzschrittmachertherapie und Elektrophysiologie, vol. 10 (4), (Dec. 1999), 248-251.
Hoffmann, E., et al., "Experience with pectoral versus abdominal implantation of a small defibrillator", European Heart Journal, vol. 19., (Jul. 1998), 1085-1098.
Park, Jeanny K., et al., "Use of an Implantable Cardioverter Defbrillator in an Eight-Month-Old Infant with Ventricular Fibrillation Arising from a Myocardial Fibroma", PACE, vol. 22, (Jan. 1999), 138-139.
U.S. Appl. No. 14/275,845, filed May 12, 2014, 38 pgs.

* cited by examiner

METHOD OF IMPLANTING AND USING A SUBCUTANEOUS DEFIBRILLATOR

RELATED APPLICATIONS

This application is a continuation of U.S. patent application Ser. No. 13/286,673, filed Nov. 1, 2011 and published as US 2012-0046705 A1 and now U.S. Pat. No. 8,577,454; which is a continuation of U.S. patent application Ser. No. 12/781,668, filed May 17, 2010 and published as US 2010-0228306 A1 and now U.S. Pat. No. 8,090,438; which is a continuation of U.S. patent application Ser. No. 11/529,671, filed Sep. 28, 2006 and now U.S. Pat. No. 7,720,534; which is a continuation of U.S. patent application Ser. No. 11/447,711, filed Jun. 6, 2006 and now U.S. Pat. No. 7,657,311; which is a continuation of U.S. patent application Ser. No. 10/790,903, filed Mar. 1, 2004 and now U.S. Pat. No. 7,076,294; which is a continuation of U.S. patent application Ser. No. 09/663,607, filed Sep. 18, 2000 and now U.S. Pat. No. 6,721,597; the entire disclosures of which are all incorporated herein by reference.

This application is related to U.S. patent application Ser. No. 09/663,606, filed Sep. 18, 2000, now U.S. Pat. No. 6,647,292 and titled UNITARY SUBCUTANEOUS ONLY IMPLANTABLE CARDIOVERTER-DEFIBRILLATOR AND OPTIONAL PACER, the entire disclosure of which is herein incorporated by reference.

FIELD

The present invention relates to an apparatus and method for performing electrical cardioversion/defibrillation and optional pacing of the heart via a totally subcutaneous non-transvenous system.

BACKGROUND

Defibrillation/cardioversion is a technique employed to counter arrhythmic heart conditions including some tachycardias in the atria and/or ventricles. Typically, electrodes are employed to stimulate the heart with electrical impulses or shocks of a magnitude substantially greater than pulses used in cardiac pacing.

Defibrillation/cardioversion systems include body implantable electrodes and are referred to as implantable cardioverter/defibrillators (ICDs). Such electrodes can be in the form of patches applied directly to epicardial tissue, or at the distal end regions of intravascular catheters, inserted into a selected cardiac chamber. U.S. Pat. Nos. 4,603,705; 4,693,253; 4,944,300; and 5,105,810, the disclosures of which are all incorporated herein by reference, disclose intravascular or transvenous electrodes, employed either alone or in combination with an epicardial patch electrode. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,467,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of the pulse monitor/generator surgically implanted into the abdomen and subcutaneous electrodes implanted in the thorax. This system is far more complicated to use than current ICD systems using transvenous lead systems together with an active can electrode, and therefore, it has no practical use. It has, in fact, never been used because of the surgical difficulty of applying such a device (3 incisions), the impractical abdominal location of the generator and the electrically poor defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that are still require significant surgery.

As ICD therapy becomes more prophylactic in nature and used in progressively less ill individuals, especially children at risk of cardiac arrest, the requirement of ICD therapy to use intravenous catheters and transvenous leads in an impediment to very long term management as most individuals will begin to develop complications related to lead system malfunction sometime in the 5- to 10-year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, is not without their chronic patient management limitations in those with life expectancies of greater than 5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of automatic external defibrillator (AED) therapy. AEDs employ the use of cutaneous patch electrodes to effect defibrillation under the direction of bystander user who treats the patient suffering from V-Fib. AEDs can be as effective as an ICD if applied to the victim promptly within 2 to 3 minutes.

AED therapy has great appeal as a tool for diminishing the risk of death in public venues such as in air flight. However, an AED must be used by another individual, not the person suffering from the potentially fatal rhythm. It is more of a public health tool than a patient-specific tool like an ICD. Because greater than 75% of cardiac arrests occur in the home, and over half occur in the bedroom, patients at risk of cardiac arrest are often alone or asleep and cannot be helped in time with an AED. Moreover, its success depends to a reasonable degree on an acceptable level of skill and calm by the bystander user.

What is needed therefore, especially for children and for prophylactic long term use, is a combination of the two forms of therapy which would provide prompt and near-certain defibrillation, like an ICD, but without the long-term adverse sequelae of a transvenous lead system while simultaneously using most of the simpler and lower cost technology of an AED. We call such a device a subcutaneous only ICD (S-ICD) and is described in detail below.

SUMMARY

The preferred embodiment for the subcutaneous only ICD (S-ICD) with optional pacing consists of five basic components: 1) an electrically active canister housing a battery supply, capacitor and operational circuitry wherein the housing serves as an electrode and replaces one conventional lead of the prior art systems; 2) one or more subcutaneous combined high voltage/sense/pace electrodes emanating from the S-ICD housing; 3) sense circuitry suitable to an ICD or AED V-FIB detection algorithm; 4) an application system for simple insertion of the subcutaneous lead; and 5) a cutaneous test system designed to estimate the best location of the S-ICD for each patient. Therefore, no transvenous lead system is necessary, eliminating a significant impediment to broader scale prophylactic use and especially use in children.

The active canister housing will provide energy and voltage intermediate to that available with ICD and AEDs. The typical maximum voltage necessary for ICDs using most biphasic waveforms is approximately 750 V and associated maximum energy of approximately 40 J. The typical maximum voltage necessary for AEDs is approximately 2000-5000 V with an associated maximum energy of approximately 150-360 J. The S-ICD of the present invention will use voltages in the range of 800 to 2000 V and associated with energies of approximately 40-150 J. The canister could be employed as either a cathode or an anode.

In the preferred embodiment, only one subcutaneous high voltage electrode, of opposite polarity to the canister, will be used but no limit is placed on the number of subcutaneous electrodes that may be required to achieve optimal S-ICD function. The subcutaneous electrode, composed of silicone or polyurethane insulation, will have a minimum of 1 electrode but, in the preferred embodiment, will have 3: a high voltage, low-impedance coil electrode approximately 5-10 cm in length and two low voltage, high impedance sense electrodes at the tip. The spacing of the sense electrodes will be approximately 4 cm to provide a reasonable QRS signal from a subcutaneous extracardic sampling location but may be of variable length to allow for sense optimization. In the preferred embodiment, the sense electrodes are placed proximal to the high voltage lead, contrary to typical transvenous ICD lead systems, but alternative locations are allowed.

The sense circuitry in the preferred embodiment is designed to be highly sensitive and specific to the presence or absence of life threatening ventricular arrhythmias only. Features of the detection algorithm are programmable, but the algorithm is focused on the detection of V-Fib and high rate ventricular tachycardia (V-Tach) of greater than 240 bpm. This type of cardioverter-defibrillator is not necessarily designed to replace ICD therapy for those with pre-identified problems of V-Tach/V-Fib or even atrial fibrillation, but is particularly geared to use as a prophylactic, long-term device, used for the life of the patient at risk of his/her first V-Fib/V-Tach event. The device of the present invention may infrequently be used for an actual life-threatening event but can be employed in large populations of individuals at modest risk and with modest cost by physicians of limited experience. Consequently, the preferred embodiment of the present invention focuses only on the detection and therapy of the most malignant rhythm disorders. As part of the detection algorithm's applicability to children, the upper rate range is programmable upward for use in children, who are known to have more rapid supraventricular tachycardias as well as more rapid ventricular tachycardias compared to adults.

The incision to apply the device of the present invention can be anywhere on the thorax although in the preferred embodiment, the device of the present invention will be applied in the left anterior mid-clavicular line approximately at the level of the mammary crease beneath the left areolus. The S-ICD can be placed subcutaneously as any ICD is currently placed. One critical difference is the high voltage/sense lead is placed totally subcutaneously with a specially designed curved introducer set, through which local anesthetic can be delivered, if necessary, followed by insertion of the lead system via the same incision used for generator insertion. The lead, however, unlike the generator, is directed laterally and posterior for positioning of the lead in the posterior thoracic region, ideally in the left posterior axillary line at the level of the inferior scapula tip. Such a lead position will allow for a good transthoracic current delivery vector as well as positioning of the proximally positioned sense bipole in a good location for identification of the QRS. There is no transvenous component.

The final component of the S-ICD is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacing to optimize signal detection in order to allow for variable sense bipole spacings on leads of different length and electrode spacing and configuration.

BRIEF DESCRIPTION OF THE DRAWINGS

For a better understanding of the invention, reference is now made to the drawings where like numerals represent similar objects throughout the figures where.

DETAILED DESCRIPTION

Figure 1:
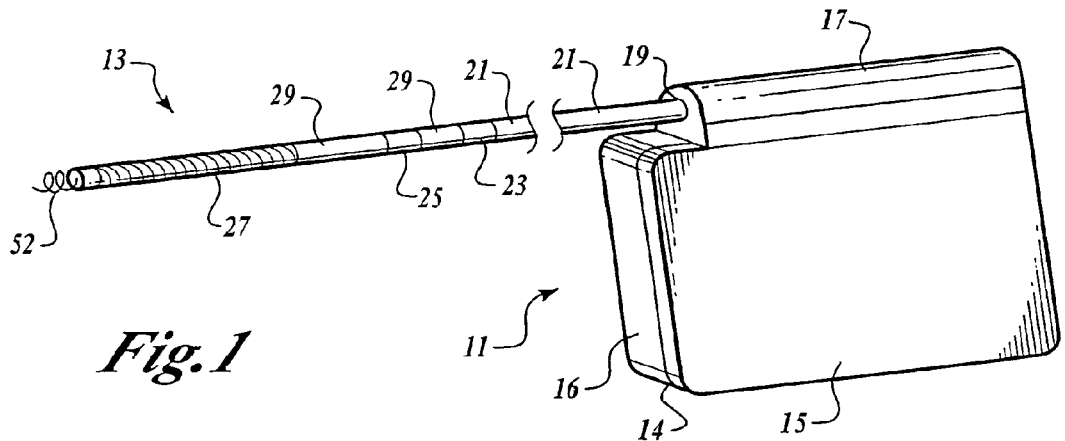
FIG. 1 is a schematic view of a Subcutaneous ICD (S-ICD) of the present invention.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In the preferred embodiment, a 100 uF biphasic wave form is used of approximately 10-20 ms total duration and with the initial phase containing approximately ⅔ of the energy, however, any type of wave form can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli will be biphasic in the preferred embodiment and similar in pulse amplitude to that used for conventional transthoracic pacing.

The same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also, the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Cardioverter and Defibrillator, Computers in Cardiology (1986) pp 167-170. Detection can be provided via R-R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form a rate detection algorithm that triggers charging of the capacitor once the ventricular rate exceeds some predetermined level for a fixed period of time: for example, if the ventricular rate exceeds 240 bpm on average for more that 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R-R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patient is not respiring and this lack of respiration can be used to confirm the QRS findings of cardiac arrest. The same technique can be used to provide information about the respiratory rate or estimate cardiac output as described in U.S. Pat. Nos. 6,095,987; 5,423,326; and 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way, the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long-term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of the preferred embodiment is that the charge time for the therapy intentionally be relatively long to allow capacitor charging within the limitations of device size. Examples of small ICD housings are disclosed in U.S. Pat. Nos. 5,957,956 and 5,405,363, the entire disclosures of which are herein incorporated by reference.

Figure 2:
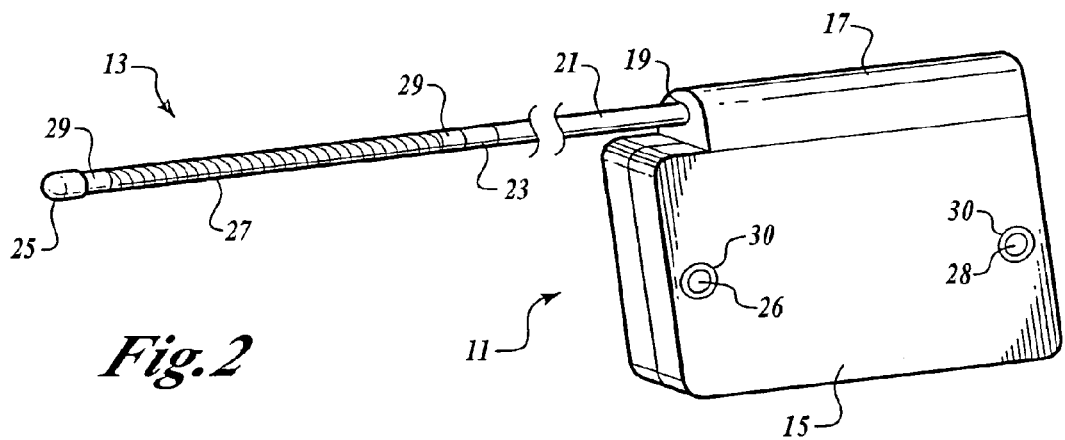
FIG. 2 is a schematic view of an alternate embodiment of a subcutaneous electrode of the present invention.
Figure 3:
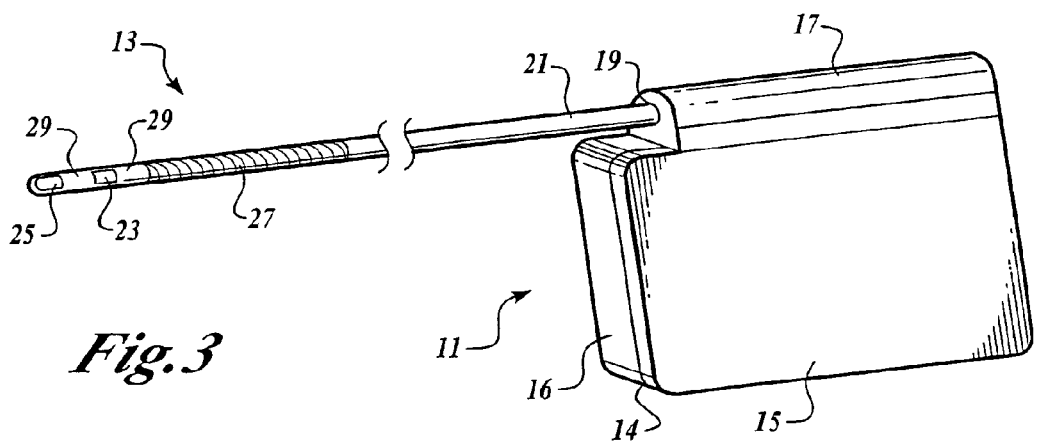
FIG. 3 is a schematic view of an alternate embodiment of a subcutaneous electrode of the present invention.

Different subcutaneous electrodes 13 of the present invention are illustrated in FIGS. 1-3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5-10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment, the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention. For example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The S-ICD of the present invention uses maximum voltages in the range of about 800 to about 2000 Volts and is associated with energies of about 40 to about 150 Joules. The capacitance of the S-ICD could range from about 50 to about 200 microfarads.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life-threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Figure 4:
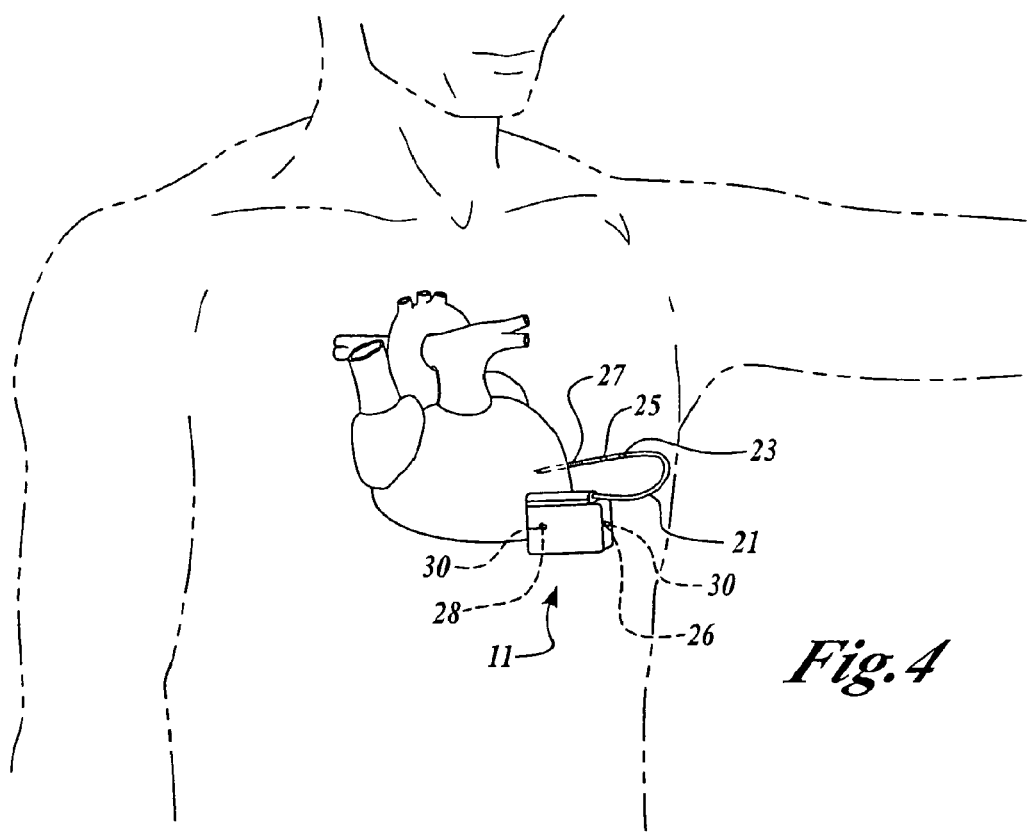
FIG. 4 is a schematic view of the S-ICD and lead of FIG. 1 subcutaneously implanted in the thorax of a patient.

Turning now to FIG. 4, the optimal subcutaneous placement of the S-ICD of the present invention is illustrated. As would be evident to a person skilled in the art, the actual location of the S-ICD is in a subcutaneous space that is developed during the implantation process. The heart is not exposed during this process and the heart is schematically illustrated in the Figures only for help in understanding where the canister and coil electrode are three-dimensionally located in the thorax of the patient. The S-ICD canister with the active housing is located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line, ideally just lateral to the left scapula. This way the canister and subcutaneous cardioversion/defibrillation electrode provide a reasonably good pathway for current delivery to the majority of the ventricular myocardium.

Figure 5:
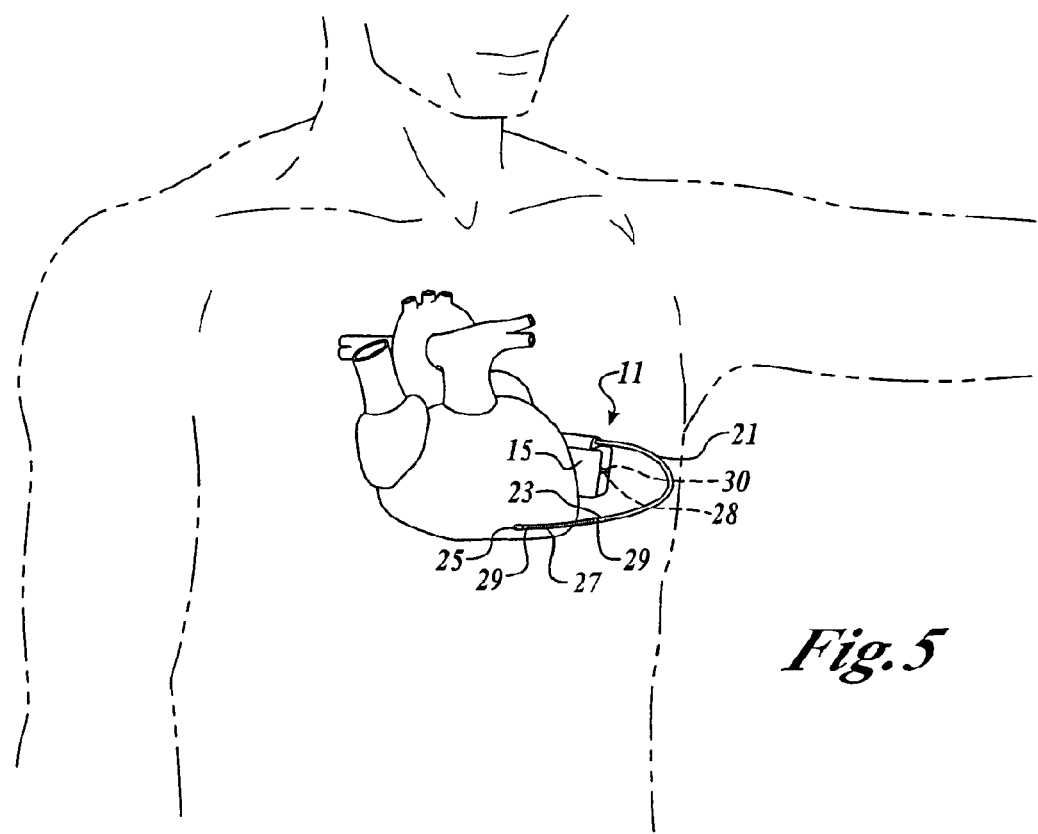
FIG. 5 is a schematic view of the S-ICD and lead of FIG. 2 subcutaneously implanted in an alternate location within the thorax of a patient.
Figure 6:
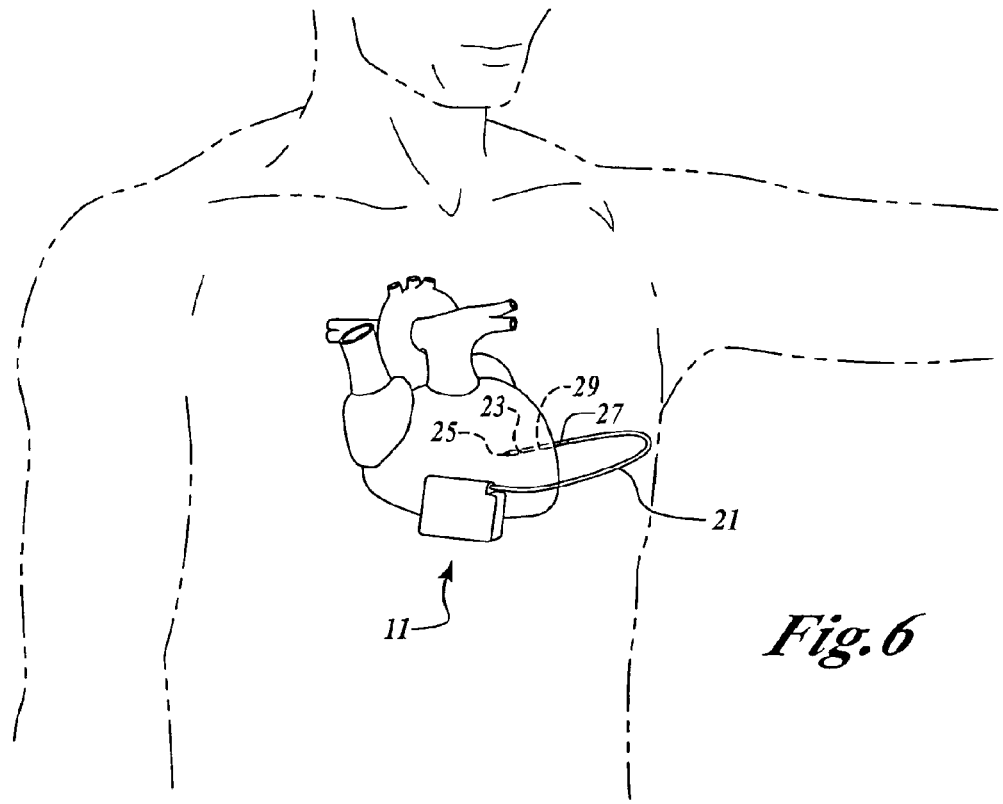
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
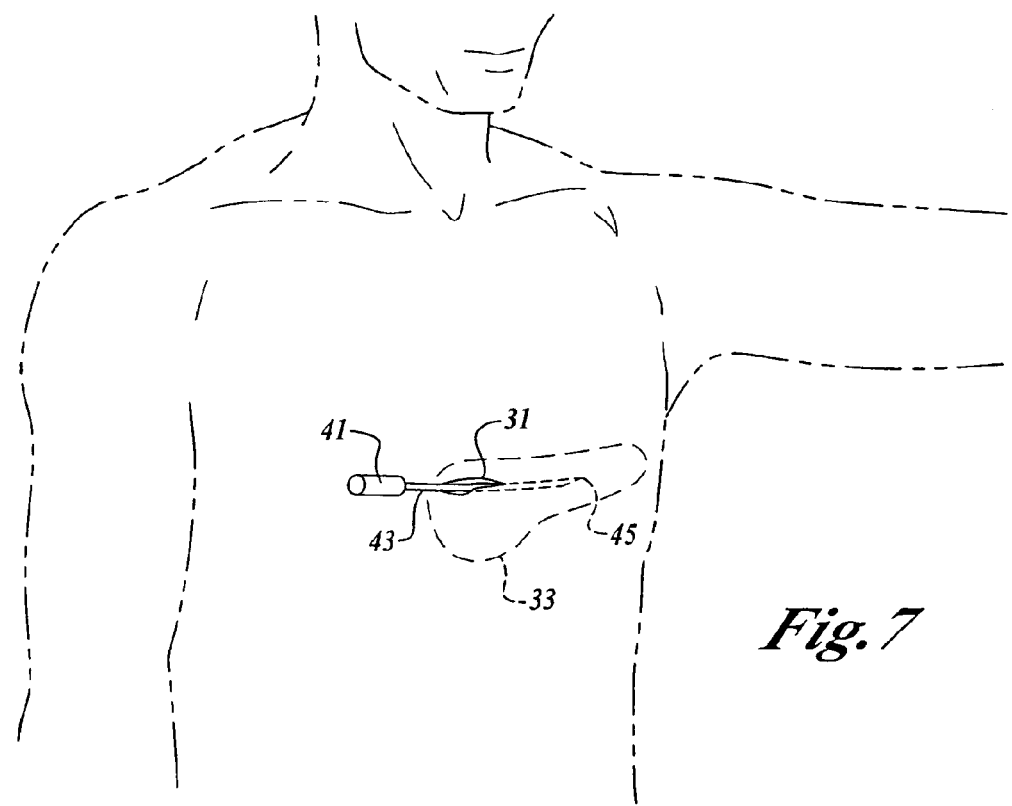
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonable by the implanting physician although in the preferred embodiment, the S-ICD of the present invention will be applied in this region. A subcutaneous pathway 33 is then created medially to the inframammary crease for the canister and posteriorly to the left posterior axillary line lateral to the left scapula for the lead.

Figure 8:
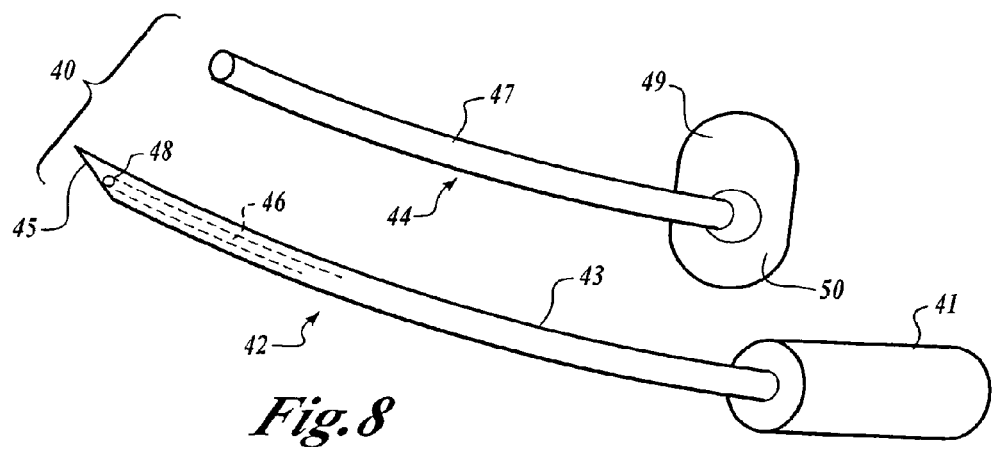
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
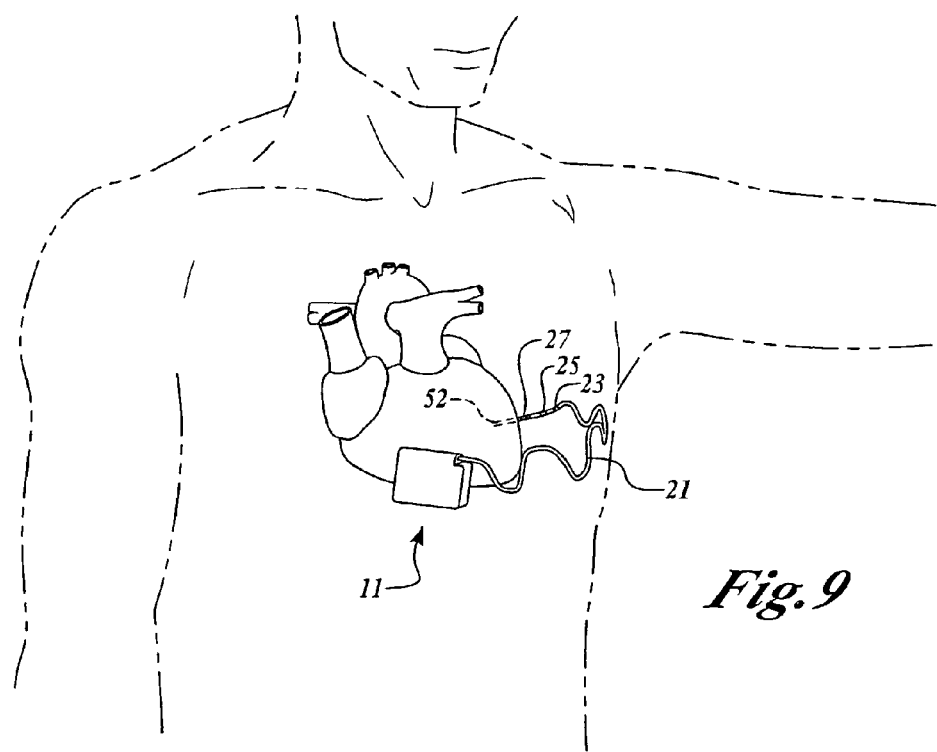
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that the problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21 however is no longer placed in a taut configuration. Instead, the lead is serpiginously placed with a specially designed introducer trocar and sheath such that it has numerous waves or bends. As the child grows, the waves or bends will straighten out, lengthening the lead system while maintaining proper electrode placement. Although it is expected that fibrous scarring, especially around the defibrillation coil, will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
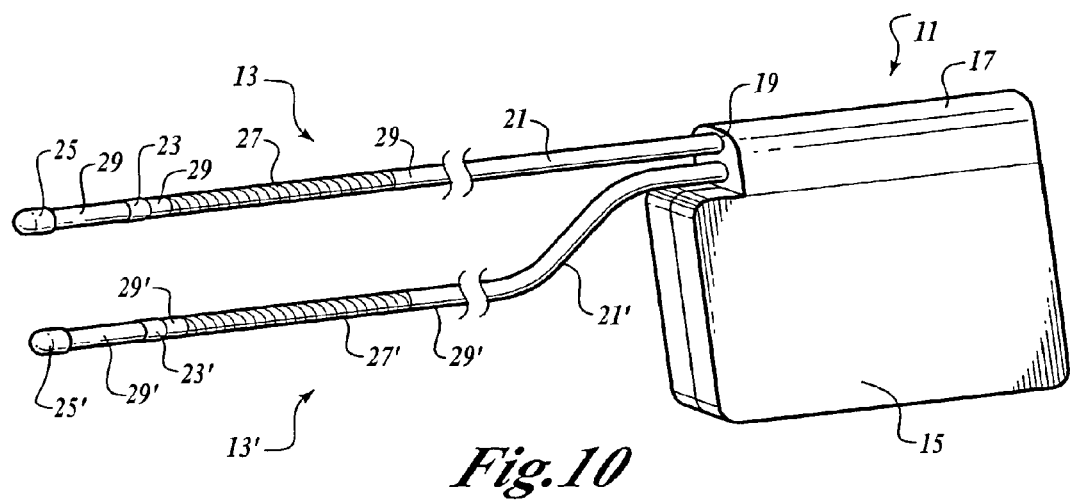
FIG. 10 is a schematic view of an alternate embodiment of an S-ICD of the present invention.
Figure 11:
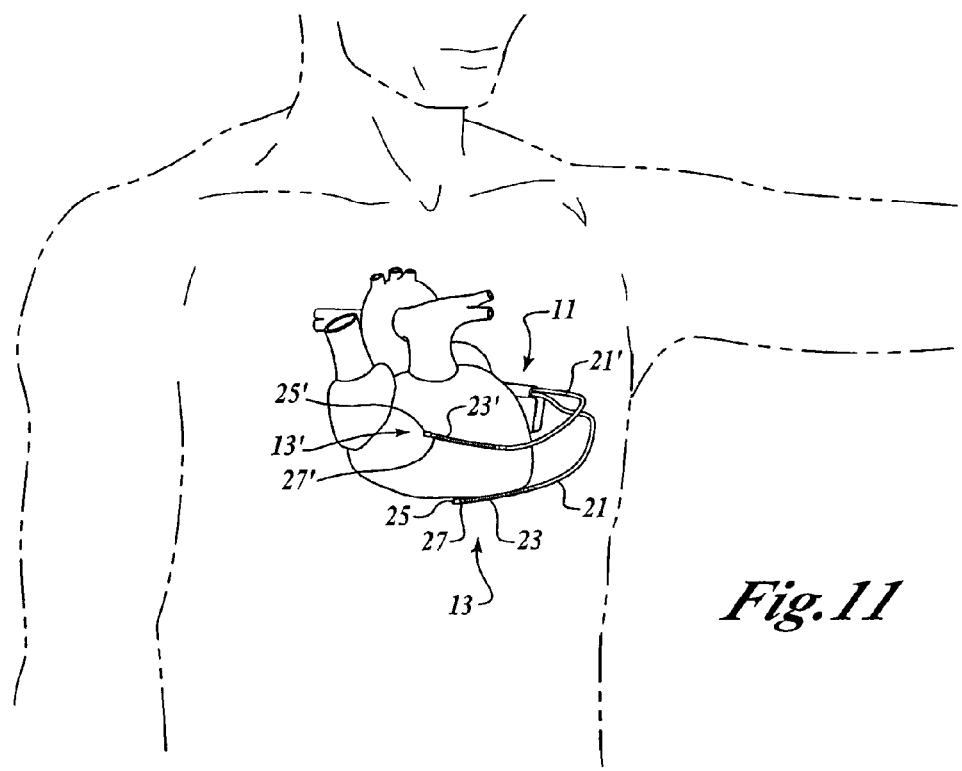
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment, the cardioversion/defibrillation energy is delivered between the active surface of the canister and the two coil electrodes 27 and 27'. Additionally provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
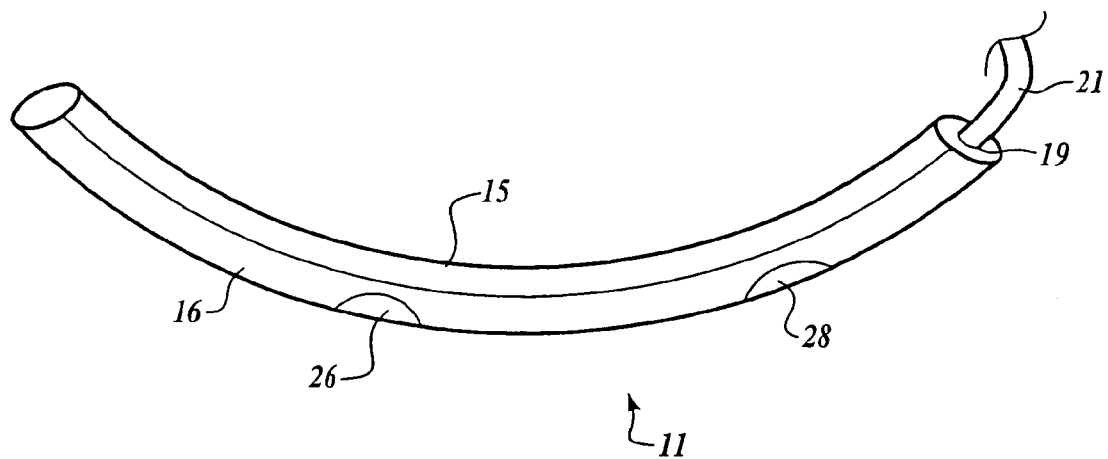
FIG. 12 is a schematic view of a yet a further embodiment where the canister of the S-ICD of the present invention is shaped to be particularly useful in placing subcutaneously adjacent and parallel to a rib of a patient.
Figure 13:
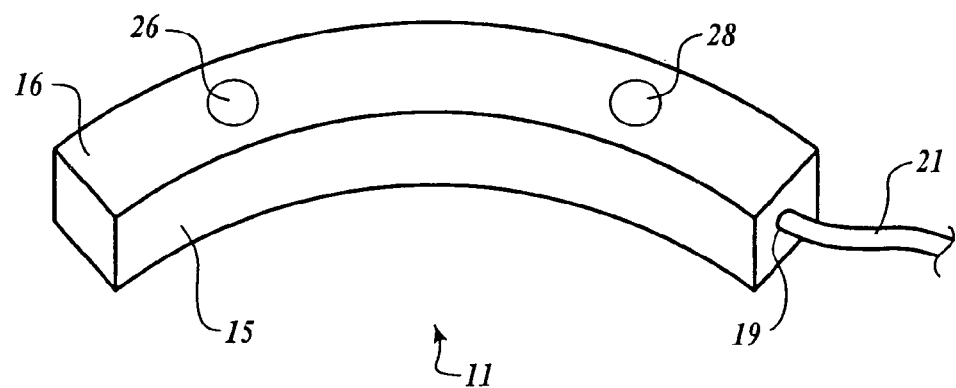
FIG. 13 is a schematic of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm with about 1 cm being presently preferred. Alternatively, instead of having a circular cross-sectional area, the canister could have a rectangular or square cross-sectional area as illustrated in FIG. 13 without falling outside of the scope of the present invention. The length of the canister can vary depending on the size of the patient's thorax. Currently, the canister is about 5 cm to about 15 cm long with about 10 cm being presently preferred. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 25 cm depending on the size of the patient. Additionally, the radius of the curvature need not be uniform throughout the canister such that it can be shaped closer to the shape of the ribs. The canister has an active surface 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface or the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However, other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

The S-ICD device and method of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A method of treating a patient comprising implanting a subcutaneous-only defibrillator comprising a subcutaneous lead having a single high voltage electrode and a plurality of sense electrodes and a canister coupled to the subcutaneous lead and including at least a high voltage electrode, the subcutaneous lead being formed of insulation having conductors therethrough and electrodes thereon, the single high voltage electrode being approximately 5-10 cm in length, wherein implanting is performed by implanting the canister at the left anterior mid-clavicular line beneath the left areolus, directing a curved introducer laterally and posteriorly for positioning the subcutaneous lead, introducing the subcutaneous lead to a left posterior thoracic position and placing the subcutaneous-only defibrillator at the incision location, wherein the subcutaneous-only defibrillator comprises sense circuitry designed to be sensitive to detection of ventricular fibrillation or tachyarrhythmia at rates above 240 bpm.

2. The method of claim 1 wherein the insulation of the subcutaneous lead is made of silicone.

3. The method of claim 1 wherein the insulation of the subcutaneous lead is made of polyurethane.

4. The method of claim 1 wherein the subcutaneous lead is implanted such that it is positioned in the left posterior axillary line at the level of the inferior scapula tip.

5. The method of claim 1 wherein the implantation is performed in a subcutaneous-only manner such that there is no transvenous component and no contact with the heart.

6. A cutaneous test electrode system designed to simulate a subcutaneous high voltage shock and QRS rhythm detection system of an implantable subcutaneous defibrillator which has a canister and lead including a defibrillation electrode and sensing electrodes comprising:
   a cutaneous patch electrode of similar surface area and impedance to that of the canister;
   a plurality of cutaneous strip electrodes each having a defibrillation strip and button electrodes at different bipole spacings allowing testing of leads of different length and electrode spacing and configuration;
   wherein the cutaneous test electrode system is configured for estimating the best location of the implantable subcutaneous defibrillator for individual patients.

* * * * *